United States Patent [19]
Bright et al.

[11] 4,271,174
[45] Jun. 2, 1981

[54] CONTROL OF SHIPPING FEVER

[75] Inventors: David R. Bright; Robert D. Williams, both of Terre Haute, Ind.

[73] Assignee: International Minerals & Chemical Corp., Terre Haute, Ind.

[21] Appl. No.: 154,551

[22] Filed: May 29, 1980

[51] Int. Cl.³ .............................................. A61K 31/42
[52] U.S. Cl. ................................................... 424/272
[58] Field of Search ........................................ 424/272

[56] References Cited
PUBLICATIONS

The Merck Index-9th edit. (1976) pp. 360 & 361.

*Primary Examiner*—Sam Rosen
*Attorney, Agent, or Firm*—Robert H. Dewey

[57] ABSTRACT

A method for prophylactically and therapeutically treating mammals for the bacterial aspects of shipping fever caused by Pasteurella species prior to exposure, during incubation or during the symptomatic phase comprising parenterally administering to the mammal cycloserine in a dose sufficient to alleviate symptoms of shipping fever.

3 Claims, No Drawings

CONTROL OF SHIPPING FEVER

BACKGROUND OF THE INVENTION

This invention relates to a method for control of the bacterial aspects of shipping fever. In a particular aspect, this invention relates to a method for control of the bacterial aspects of shipping fever when the bacteria are Pasteurella species.

Shipping fever is the name commonly used for a multi-faceted disease syndrome usually associated with the transportation, concentration and confinement of animals, especially mammals such as cattle, sheep, goats, horses, similar wild species, and the like. This syndrome, which annually costs cattle producers millions of dollars in the United States alone, is most commonly encountered in cattle and sheep which have been recently weaned, transported to market, sorted and sold, and again transported to a new home, such as a farm, ranch, or feed lot. The disease can even occur in the absence of transportation or other stressful circumstances. Accordingly, while the stress adaptation response can be a significant and predisposing factor in the development of shipping fever, certain microorganisms can, under conditions of adequate exposure, cause the diverse facets of the disease complex independent of the stress adaption response.

Shipping fever is an acute respiratory disease clinically characterized by fever, depression, anorexia, nasal discharge, acute inflammation of the air-ways, and pneumonia. There may be several species of bacteria involved, and also one or more viruses. Of the bacteria, species of Pasteurella such as *P. multocida* or *P. hemolytica* are regarded by most authorities as being the most important. It is, therefore, advantageous to provide a suitable antibacterial agent for the control of shipping fever in cattle, sheep, horses and the like.

SUMMARY OF THE INVENTION

It is an object of this invention to provide a method for control of shipping fever in mammals.

It is another object of this invention to provide a method for controlling the bacterial aspects of shipping fever caused by species of Pasteurella.

Other objects of this invention will be apparent to those skilled in the art from the disclosure herein.

It is the discovery of this invention to provide a method for prophylactically and therapeutically treating mammals for the bacterial aspects of shipping fever caused by Pasteurella species prior to exposure, during incubation or during the symptomatic phase comprising parenterally administering to the mammal cycloserine in a dosage sufficient to alleviate the symptoms of shipping fever.

DETAILED DISCUSSION

Cycloserine is a well-known antibiotic and is commercially available. It is effective in treating the bacterial aspects of shipping fever in cattle, sheep, horses, and other ruminant mammals, especially when the bacteria involved are Pasteurella, such as *P. multocida* or *P. hemolyticus*.

Cycloserine can be administered either prophylactically or therapeutically. Administration can be started immediately prior to transportation and continued throughout the period of stress, or administration can be delayed until the appearance of symptoms. In the latter case, treatment is started promptly when the clinical symptoms of shipping fever become apparent and is continued until symptoms have subsided satisfactorily. Generally treatment will be continued for five days or longer. A pharmaceutically effective dose sufficient to alleviate the symptoms is administered. Generally a dose of 2–4 mg per pound of body weight administered once or twice daily is sufficient.

Cycloserine is administered parenterally by any art-recognized method, of which many are known. For example, it can be administered subcutaneously, intravenously, intramuscularly or in the form of a pellet which is absorbed gradually as is known in the art. The preferred method of administration is intramuscularly as a sterile, aqueous solution.

The invention will be better understood with reference to the following examples. It is to be understood that the examples are intended only to illustrate the invention and it is not intended that the invention be limited thereby.

EXAMPLE 1

A pure culture of *Pasteurella multocida* (strain 1062, sero-type A:3) was obtained from the NationaL Animal Disease Laboratory, Ames, Iowa. Stock cultures were prepared and tested in lambs known to be susceptible to *P. multocida* in order to confirm virulence. Challenge inoculum was prepared in tripticase soy broth (no dextrose) containing 10% horse serum. A 20 hour culture which contained $8.8 \times 10^8$ colony forming units (CFU's) of *P. multocida* was diluted 1:5 with 1% sterile peptone. Retitration of diluted culture indicated it contained $1.6 \times 10^8$ CFU's of *P. multocida* per ml.

A group of 25 test lambs were obtained locally from a flock (Sealine) which had previously been tested (via pulmonary challenge) for susceptibility to *P. multocida*. The lambs were randomly allotted by sex and weight into five pens of five lambs each. All lambs were fed a good quality alfalfa hay and a non-medicated grain mix. Automatic nipple waterers provided a continuous source of fresh water throughout the test. Individual pens (concrete floors) were scraped daily.

Each lamb was inoculated with a total of 0.2 ml culture ($3.2 \times 10^7$ CFU's) by securing the lamb by injecting 0.1 ml of culture directly into each major diaphragmatic lung lobe. The point of needle insertion was between the fourth to fifth most posterior rib about three inches ventral to the spinal column. Wool was clipped over the injection site to facilitate injection.

Initial clinical signs of pasteurellosis consisted of watery nasal discharge (later sometimes became mucoid) accompanied by coughing (exaggerated after running). More acute cases were characterized by anorexia, ataxia, dyspnea and depression. The watery nasal discharge generally appeared 2 to 5 days post-infection (average 3.6 days). Treatment was initiated on the fourth day post-infection when 87% of the total lambs showed clinical signs of pasteurellosis. Treatment was continued for five days. On the 27th day after inoculation, the test was terminated and all surviving animals were sacrificed.

The lambs in pens 1 and 2 were treated intramuscularly with a solution of cycloserine (CS) (200 mg/ml) at a dosage of 4 mg/lb, once a day for pen 1, and twice a day for pen 2. There were no deaths in either group after treatment started, but prior to treatment, one lamb from pen 1 died. Clinical improvement of symptoms was observed during treatment.

The lambs in pens 3 and 4 were treated intramuscularly with a solution of CS (100 mg/ml) at a dosage of 2 mg/lb, once a day for pen 3 and twice a day for pen 4. One lamb from each pen had died before treatment started and one lamb from pen 3 died during the test.

The lambs in pen 5 were untreated. Two of the five died during the test.

It was concluded from the results of the test that cycloserine is an effective therapeutic drug for induced respiratory disease associated with *Pasteurella multocida* in lambs.

EXAMPLE 2

The experiment of Example 1 is repeated in all essential details except that calves are substituted for lambs. The cycloserine is effective against the disease in calves.

EXAMPLE 3

The experiment of Example 1 is repeated in all essential details except that colts are substituted for lambs. The cycloserine is effective against the disease in colts.

EXAMPLE 4

The experiment of Example 1 is repeated in all essential details except that kids are substituted for lambs. The cycloserine is effective against the disease in kids.

We claim:

1. A method for therapeutically treating mammals for the bacterial aspects of shipping fever caused by Pasteurella species, during incubation or during the symptomatic phase comprising parenterally administering to the mammal cycloserine in a dose sufficient to alleviate symptoms of shipping fever.

2. The method of claim 1 wherein cycloserine is administered at a dosage of 2-4 mg/lb of animal once daily.

3. The method of claim 1 wherein cycloserine is administered at a dosage of 2-4 mg/lb of animal twice daily.

* * * * *